US006518255B2

(12) United States Patent
Rosengart et al.

(10) Patent No.: US 6,518,255 B2
(45) Date of Patent: *Feb. 11, 2003

(54) MULTIPLE SITE DELIVERY OF ADENOVIRAL VECTOR DIRECTLY INTO MUSCLE FOR THE INDUCTION OF ANGIOGENESIS

(75) Inventors: Todd K. Rosengart, Tenafly, NJ (US); Ronald G. Crystal, Potomac, MD (US)

(73) Assignee: Cornell Research Foundation, Inc., Ithaca, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/357,010

(22) Filed: Jul. 19, 1999

(65) Prior Publication Data

US 2001/0041679 A1 Nov. 15, 2001

Related U.S. Application Data

(63) Continuation of application No. PCT/US98/01638, filed on Jan. 29, 1998, and a continuation of application No. 08/801,352, filed on Feb. 19, 1997, now Pat. No. 5,846,225.
(60) Provisional application No. 60/036,601, filed on Jan. 29, 1998, and provisional application No. 60/071,156, filed on Jan. 13, 1998.

(51) Int. Cl.[7] .................. A61K 48/00; A61K 35/00; C12N 15/09

(52) U.S. Cl. .................. 514/44; 424/93.1; 424/93.2; 435/455

(58) Field of Search .................. 514/44; 424/93.1, 424/93.2; 435/455

(56) References Cited

U.S. PATENT DOCUMENTS

| 510,413 | A | 12/1893 | Dolge |
| 2,551,902 | A | 5/1951 | Rieck |
| 2,670,673 | A | 3/1954 | Gordon et al. |
| 3,467,096 | A | 9/1969 | Horn |
| 3,572,336 | A | 3/1971 | Hershberg |
| 3,595,231 | A | 7/1971 | Pistor |
| 4,150,669 | A | 4/1979 | Latorre |
| 4,167,179 | A | 9/1979 | Kirsch |
| 5,219,739 | A | 6/1993 | Tischer et al. |
| 5,240,848 | A | 8/1993 | Keck et al. |
| 5,244,460 | A | 9/1993 | Unger et al. |
| 5,273,525 | A | 12/1993 | Hofmann |
| 5,290,258 | A | 3/1994 | Ennis, III et al. |
| 5,332,671 | A | 7/1994 | Ferrara et al. |
| 5,335,670 | A | 8/1994 | Fishman |
| 5,338,840 | A | 8/1994 | Bayne et al. |
| 5,417,683 | A | 5/1995 | Shiao |
| 5,532,343 | A | 7/1996 | Bayne et al. |
| 5,792,453 | A | * 8/1998 | Hammond et al. ...... 424/93.21 |
| 5,846,225 | A | 12/1998 | Rosengart et al. |
| 5,851,806 | A | * 12/1998 | Kovesdi et al. .......... 435/93.41 |
| 6,121,246 | A | 9/2000 | Isner ......................... 536/23.1 |
| 6,228,844 | B1 | * 5/2001 | Wolff et al. ................... 514/44 |

FOREIGN PATENT DOCUMENTS

| EP | 476 983 | 3/1992 |
| EP | 506 477 | 9/1992 |
| EP | 550 296 | 7/1993 |
| JP | 1038100 | 2/1989 |
| JP | 2117698 | 5/1990 |
| JP | 2279698 | 11/1990 |
| JP | 3178996 | 8/1991 |
| WO | WO 95/24473 | 9/1995 |
| WO | WO 96/12406 | 5/1996 |

OTHER PUBLICATIONS

Miller FASEB J., vol. 9, pp. 190–199, 1995.*
Deonarain Expert Opin. Ther. Pat., vol. 8, pp. 53–69, 1998.*
Verma Nature, vol. 389, pp. 239–242, Sep. 1997.*
Crystal Science, vol. 270, p. 404–410, 1995.*
Isner et al., The Lancet, vol. 348, pp. 370–374, Aug. 1996.*
Magovern et al., Ann. Thorac. Surg., vol. 62, pp. 425–434, 1996.*
Magovern et al., Human Gene Therapy, vol. 8, pp. 215–227, Jan. 1997.*
Mühlhauser et al., Circ. Res., vol. 77, pp. 1077–1086, 1995.*
Kass–Eisler et al., Quantitative determination of adenovirus–mediated gene delivery to rat cardiac myocytes in vitro and in vivo, 1993, Proc. Natl. Acad. Sci. USA, vol. 90, pp. 11498–11502.*
Quantin et al., Adenovirus as an expression vector in muscle cells in vivo, 1992, Proc. Natl. Acad. Sci. USA, vol. 89, pp. 2581–2584.*
French, Ph. D et al., Direct in vivo gene transfer into procine myocardium using replication–deficient adenoviral vectors, 1994, Circulation, vol. 90, pp. 2414–2424.*

(List continued on next page.)

Primary Examiner—Michael C. Wilson
(74) Attorney, Agent, or Firm—Leydig, Voit & Mayer, Ltd.

(57) ABSTRACT

The present invention provides a method for enhancing the level of perfusion of blood to a target tissue, treating a target tissue suffering from or at risk of suffering from ischemic damage, inducing angiogenesis in a target tissue, and/or inducing collateral blood vessel formation in a target tissue affected by or at risk of being affected by a vascular occlusion. The present inventive method comprises administering to the target tissue a dose of a pharmaceutical composition comprising (a) a pharmaceutically acceptable carrier and (b) an adenoviral vector comprising a DNA encoding an angiogenic peptide, such that the level of perfusion of blood to the target tissue is enhanced, the dose has a therapeutic or prophylactic effect on the target tissue, angiogenesis is induced in the target tissue, and/or the adenoviral vector contacts a region including the source, the terminus, and an area therebetween for the collateral blood vessel formation, and collateral blood vessel formation is induced.

96 Claims, No Drawings

OTHER PUBLICATIONS

Muhlhauser et al., VEGF 165 expressed by a replication–deficient recombinant adenovirus vector induces angiogenesis in vivo, 1995, Circ. Res., vol. 77, pp. 1077–1086.*

Banai et al., *Circulation, 89* (5), 2183–2189 (May 1994).

Mack et al., *The Journal of Thoracic and Cardiovascular Surgery, 155* (1), 168–177 (Jan. 1998).

Magovern et al., *Annals of Thoracic Surgery, 62*, 425–434 (1996).

Magovern et al., *Human Gene Therapy, 8* (2), 215–227 (Jan. 20, 1997).

Mühlhauser et al., *Circulation Research, 77* (6), 1077–1086 (1995).

Mühlhauser et al., *Human Gene Therapy, 6*, 1457–1465 (1995).

Poltorak et al., *The Journal of Biological Chemistry, 272* (11), 7151–7158 (Mar. 14, 1997).

Pearlman et al., *Nature Medicine, 1* (10), 1085–1089 (Oct. 1995).

Raeburn et al., *Business Week*, 48 (Nov. 24, 1997).

Rajanayagam et al., *Circulation, 94*, I–646 (Abstract 3773) (Oct. 15, 1996).

Soker et al., *The Journal of Biological Cehmistry, 271* (10), 5761–5767 (Mar. 8, 1996).

* cited by examiner

MULTIPLE SITE DELIVERY OF ADENOVIRAL VECTOR DIRECTLY INTO MUSCLE FOR THE INDUCTION OF ANGIOGENESIS

CROSS-REFERENCE TO RELATED PATENT APPLICATIONS

This patent application is a continuation of copending International Application No. PCT/US98/01638, filed Jan. 29, 1998, which designates the U.S., and which claims the benefit of U.S. Provisional Patent Application No. 60/036,601, filed Jan. 29, 1998, and U.S. Provisional Patent Application No. 60/071,156, filed Jan. 13, 1998, and is a continuation of U.S. patent application Ser. No. 08/801,352, filed Feb. 19, 1997, issued as U.S. Pat. No. 5,846,225.

TECHNICAL FIELD OF THE INVENTION

The present invention relates to a method for enhancing the level of perfusion of blood to a target tissue, a method for treating a target tissue suffering from or at risk of suffering from ischemic damage, and a method of inducing angiogenesis in a target tissue.

BACKGROUND OF THE INVENTION

Angiogenesis, the growth of new blood vessels, is a complex process involving the disruption of vascular basement membranes, migration and proliferation of endothelial cells, and subsequent blood vessel formation and maturation. Several mediators are known to elicit angiogenic responses, and administration of these mediators promotes revascularization of ischemic tissues. Vascular endothelial growth factor (VEGF protein) is one of the most specific of the known angiogenic mediators due to localization of its receptors almost exclusively on endothelial cells. Receptors for VEGF are upregulated under ischemic conditions, and the administration of recombinant VEGF augments the development of collateral vessels and improves function in peripheral and myocardial ischemic tissue.

However, delivery of VEGF protein remains a significant challenge. The half-life of VEGF protein is very short; the administration of high doses of VEGF protein is associated with hypotension, and systemic administration of VEGF protein can cause promiscuous induction of angiogenesis in tissues other than that which has been targeted. Promiscuous induction of angiogenesis can cause blindness, increase the aggressiveness of tumor cells, and lead to a multitude of other negative side-effects. Furthermore, the quantity of VEGF protein delivered is important. If too little VEGF protein is delivered, angiogenesis will not be induced, and a significant therapeutic benefit will not be achieved. If too much VEGF protein is delivered, the formation of disorganized vasculature beds, loss of function in the affected tissue, and promiscuous angiogenesis can result.

Additionally, induction of angiogenesis via administration of liposomes and/or "naked" DNA comprising a DNA encoding an angiogenic peptide also suffer from numerous disadvantages. Specifically, both liposomal and "naked" DNA forms of delivery are less efficient than viruses at transferring genes to cells, are inefficient at integrating genes into the host genome, and are difficult to target to specific tissues.

In view of the foregoing, there exists a need for an effective method of inducing angiogenesis in a target tissue. The present invention provides such a method. These and other advantages of the present invention, as well as additional inventive features, will be apparent from the description of the invention provided herein.

BRIEF SUMMARY OF THE INVENTION

The present invention provides a method for enhancing the level of perfusion of blood to a target tissue comprising administering, via multiple applications to the target tissue, a dose of a pharmaceutical composition comprising (a) a pharmaceutically acceptable carrier and (b) an adenoviral vector comprising a DNA encoding an angiogenic peptide, such that the level of perfusion of blood to the target tissue is enhanced. Also provided is a method for treating a target tissue suffering from or at risk of suffering from ischemic damage comprising administering, via multiple applications to the target tissue, a dose of a pharmaceutical composition comprising (a) a pharmaceutically acceptable carrier and (b) an adenoviral vector comprising a DNA encoding an angiogenic peptide, such that the dose has a therapeutic or prophylactic effect on the target tissue. Further provided is a method for inducing angiogenesis in a target tissue comprising administering, via multiple applications to the target tissue, a dose of a pharmaceutical composition comprising (a) a pharmaceutically acceptable carrier and (b) an adenoviral vector comprising a DNA encoding an angiogenic peptide, such that angiogenesis is induced in the target tissue. Additionally provided is a method for inducing collateral blood vessel formation in a target tissue affected by or at risk of being affected by a vascular occlusion comprising administering to the target tissue a dose of a pharmaceutical composition comprising (a) a pharmaceutically acceptable carrier and (b) an adenoviral vector comprising a DNA encoding an angiogenic peptide, such that the adenoviral vector contacts a region including the source, the terminus, and an area therebetween for the collateral blood vessel formation, and collateral blood vessel formation is induced.

DESCRIPTION OF THE PREFERRED EMBODIMENTS

The invention may best be understood with reference to the following detailed description of the preferred embodiments. The present invention provides a method for enhancing the level of perfusion of blood to a target tissue, a method for treating a target tissue suffering from or at risk of suffering from ischemic damage, a method for inducing angiogenesis in a target tissue, and/or a method for inducing collateral blood vessel formation in a target tissue affected by or at risk of being affected by a vascular occlusion. Each of these methods involves administering, via multiple applications to the target tissue, a dose of a pharmaceutical composition comprising (a) a pharmaceutically acceptable carrier and (b) an adenoviral vector comprising a DNA encoding an angiogenic peptide, such that the level of perfusion of blood to the target tissue is enhanced, the dose has a therapeutic or prophylactic effect on the target tissue, angiogenesis is induced in the target tissue, and/or the adenoviral vector contacts a region including the source, the terminus, and an area therebetween for collateral blood vessel formation, and collateral blood vessel formation is induced.

Induction of Angiogenesis

By the term "inducing angiogenesis," it is meant that angiogenesis is either initiated or enhanced. Therefore, for example, when the target tissue is not already undergoing angiogenesis, the present method provides for the initiation of angiogenesis in the target tissue. However, when the target tissue is already undergoing angiogenesis, the present method provides a means by which the level of angiogenesis is enhanced or heightened.

Target Tissue

Any suitable tissue can be subject to administration within the context of the present invention. Preferably, the target tissue comprises receptors capable of binding the angiogenic peptide encoded by the DNA; more preferably, the target tissue comprises VEGF receptors. Most preferably, the target tissue comprises endothelial cells. Generally, the target tissue will be a part of or form a discrete organ, e.g., a muscle, such as the heart.

Typically, the target tissue will be suffering from or be at risk of suffering from ischemic damage which results when the tissue is deprived of an adequate supply of oxygenated blood. The interruption of the supply of oxygenated blood is often caused by a vascular occlusion. Such vascular occlusion can be caused by arteriosclerosis, trauma, surgical procedures, disease, and/or other indications. There are many ways to determine if a tissue is at risk of suffering ischemic damage from undesirable vascular occlusion. Such methods are well known to physicians who treat such conditions. For example, in myocardial disease these methods include a variety of imaging techniques (e.g., radiotracer methodologies such as $^{99m}$Tc-sestamibi scanning, x-ray, and MRI scanning) and physiological tests. Therefore, induction of angiogenesis in tissue affected by or at risk of being affected by a vascular occlusion is an effective means of preventing and/or attenuating ischemia in such tissue. As a result, although any suitable tissue can be targeted for the induction of angiogenesis, the target tissue is preferably one which is affected by or at risk of being affected by a vascular occlusion.

For example, the blood supply to discrete organs such as the brain, heart, pancreas, entire limbs, or generalized areas of the body, such as a foot, can be attenuated by disease, trauma, surgery, or other events. The alleviation of such attenuated blood supply regardless of its origin is contemplated by the present invention. Thus, prevention or alleviation of damage from indications such as myocardial ischemia and stroke are fully contemplated. Additionally, the planning of a surgical procedure can be predictive of the interruption of blood supply through a particular portion of a patient's vasculature. Prior treatment according to the present method can substantially improve the desired outcome of these surgeries. In that case, treatment preferably occurs about one day to about six weeks before said surgery, and more preferably about two to about fourteen days prior to surgery.

Administration of Angiogenic Vector

As previously stated, the induction of angiogenesis via the systemic administration of angiogenic peptides, such as VEGF protein, can lead to promiscuous induction of angiogenesis which, for example, can cause blindness and increase the aggressiveness of tumor cells. Therefore, in order to attenuate or prevent such negative side-effects it is desirable to induce angiogenesis only in the tissue which requires it (i.e., the target tissue).

The present invention involves the administration of an adenoviral vector comprising a DNA encoding an angiogenic peptide in a localized manner to the target tissue. While any suitable means of administering the angiogenic vector to the target tissue can be used within the context of the present invention, preferably, such a localized administration to the target tissue is accomplished by directly injecting the angiogenic vector into the target tissue or by topically applying the angiogenic vector to the target tissue.

By the term "injecting," it is meant that the angiogenic vector is forcefully introduced into the target tissue. Any suitable injection device can be used within the context of the present invention. Such injection devices include, but are not limited to, that described in U.S. Pat. No. 5,846,225, which is directed to a gene transfer delivery device capable of delivering simultaneous multiple injections. Another example of an injection device which can be used within the context of the present invention includes minimally invasive injection devices. Such devices are capable of accessing the heart, for example, through small incisions of less than 5 inches and are designed to provide injections through a single lumen, in contrast to the multiple injection device described above. To allow for the need for multiple injections with a specific geometry, a marking system can be employed so that the sites of previous injections are well delineated. Minimally invasive injection devices can comprise injector tips which are flexible and steerable to allow access via small incisions to the curved outer surface of the heart, for example, which exists at varying angles with respect to the limited aperture window required with minimally invasive surgeries.

Furthermore, the angiogenic vector can be administered to any suitable surface, either internal or external, of the target tissue. For example, with respect to directly injecting the angiogenic vector into cardiac tissue, it is contemplated that such an injection can be administered from any suitable surface of the heart (i.e., endocardially and/or epicardially). However, it is desirable that whatever means of administering the angiogenic vector is chosen, the induction of angiogenesis in non-targeted tissue is minimized.

While administration of a dose of the angiogenic vector can be accomplished through a single application (e.g., a single injection or a single topical application) to the target tissue, preferably, administration of the dose is via multiple applications of the angiogenic vector. The multiple applications can be 2, 3, 4, 5, or more applications, preferably 5 or more applications, more preferably 8 or more applications, and most preferably at least 10 (e.g., 10, 15, or 20) applications. Multiple applications provide an advantage over single applications in that they can be manipulated by such parameters as a specific geometry defined by the location on the target tissue where each application is administered. The administration of a single dose of the angiogenic vector via multiple applications can be better controlled, and the effectiveness with which any given dose is administered can be maximized. In this way, too, the undesirable effects associated with administration of a single point application of a large dose can be minimized.

The specific geometry of the multiple applications is defined by the location on the target tissue, either in two- or three-dimensional space, where each application of the angiogenic vector is administered. The multiple applications preferably are spaced such that the points of application are separated by up to about 4 cm (e.g., about 0.5–4 cm), more preferably up to about 3 cm (e.g., about 1–3 cm), and most preferably up to about 2 cm (e.g., about 1–2 cm). With respect to the specific geometry of the multiple applications in two-dimensional space, the specific geometry is defined by a plane (i.e., a cross-section of the target tissue) in which the multiple applications lie. The plane defined by the multiple applications can lie at a constant distance from the surface of the target tissue (i.e., substantially parallel to the surface of the target tissue), the depth of the plane, or, alternatively, the plane can lie at an angle with respect to the surface of the target tissue. Preferably, a single application will be administered for about every 0.5–15 cm$^2$ of the plane, more preferably for about every 1–12 cm² of the plane, and most preferably for about every 1.5–7 cm of the plane. The depth of the plane is preferably about 1–10 mm, more preferably about 2–7 mm, and most preferably about 3–5 mm. In three-dimensional space, a single application preferably is administered for up to about 50 cm³ (e.g., about 0.5–50 cm³) of target tissue, more preferably for up to about 35 cm³ (e.g., about 1–35 cm³) of target tissue, and most preferably for up to about 15 cm³ (e.g., about 3–15 cm³) of target tissue. Furthermore, the multiple applications can define any suitable pattern or specific geometry. Therefore, for example, in two-dimensional space, the multiple applications can define a square whereas in three-dimensional space the multiple applications can define a cube.

Another parameter of the multiple applications which can be manipulated is the time differential between each application. Preferably, each of the multiple applications is administered within about 10 minutes (e.g., about 0.5–10 minutes) of each other, more preferably within about 8 minutes (e.g., about 0.5–8 minutes) of each other, and even more preferably within about 6 minutes (e.g., about 1–6 minutes) of each other. Most preferably, all of the multiple applications of the single dose are administered within the aforesaid time frames. Optimally, each of the multiple applications is administered substantially simultaneously.

By manipulating both the specific geometry and the time differentials of the multiple applications, the induction of angiogenesis in non-targeted tissue can be minimized.

When administering the angiogenic vector to a target tissue which is affected by or at risk of being affected by a vascular occlusion, it is desirable that the administration is such that the angiogenic vector is able to contact a region reasonably adjacent to the source and the terminus for the collateral blood vessel formation, as well as the area therebetween, which will function as a bypass to the vascular occlusion. It is not believed to be necessary to have the angiogenic vector actually contact the precise sites of the source and the terminus for the collateral blood vessel formation. However, within the context of multiple applications of the angiogenic vector, it is desirable that the specific geometry of the multiple applications be defined to allow the angiogenic vector to contact or reach a region including the source, the terminus, and the area therebetween for the collateral blood vessel formation, preferably to actually contact the precise sites of the source and the terminus for the collateral blood vessel formation, along with the area therebetween.

Furthermore, administration of the angiogenic vector to the target tissue can be accomplished either in vivo or ex vivo. Therefore, for example, the target tissue can be removed from the recipient of the present inventive method, can be treated with the angiogenic substance, and then can be reimplanted into the recipient. Ex vivo administration of the angiogenic substance to the target tissue also helps to minimize undesirable induction of angiogenesis in non-targeted tissue.

Angiogenic Vector

As previously stated, the delivery of VEGF protein as an angiogenic substance to tissue remains a significant challenge due, in large part, to its very short half-life. However, by utilizing an adenoviral vector comprising a DNA encoding an angiogenic peptide as the angiogenic substance, it is possible to infect host cells and thereby induce the sustained, predictable, and effective production of an angiogenic peptide for about a week. After about a week, the adenoviral vector ceases to produce the angiogenic peptide and, to that extent, the present invention provides a self-terminating method of inducing angiogenesis.

Adenoviral vectors are preferred because, unlike plasmids and other viral vectors (e.g., herpes simplex virus), adenoviral vectors achieve gene transfer in both dividing and nondividing cells, with high levels of protein expression in cardiovascular relevant sites such as myocardium, vascular endothelium, and skeletal muscle. Furthermore, the gene transferred by an adenoviral vector functions in an epichromosomal position and thus carries little risk of inappropriately inserting the transferred gene into a critical site of the host genome. The adenoviral vector also is preferably deficient in at least one gene function required for viral replication. Preferably, the adenoviral vector is deficient in at least one essential gene function of the E1 region of the adenoviral genome, particularly the E1a region, more preferably, the vector is deficient in at least one essential gene function of the E1 region and part of the E3 region (e.g., an XbaI deletion of the E3 region) or, alternatively, the vector is deficient in at least one essential gene function of the E1 region and at least one essential gene function of the E4 region. However, adenoviral vectors deficient in at least one essential gene function of the E2a region and adenoviral vectors deficient in all of the E3 region also are contemplated here and are well known in the art. Adenoviral vectors deleted of the entire E4 region can elicit lower host immune responses. Suitable replication deficient adenoviral vectors are disclosed in U.S. Pat. No. 5,851,806 and PCT International Publication No. WO 95/34671. For example, suitable replication deficient adenoviral vectors include those with a partial deletion of the E1a region, a partial deletion of the E1b region, a partial deletion of the E2a region, and a partial deletion of the E3 region. Alternatively, the replication deficient adenoviral vector can have a deletion of the E1 region, a partial deletion of the E3 region, and a partial deletion of the E4 region.

Furthermore, the viral vector's coat protein can be modified so as to incorporate a specific protein binding sequence, as described in U.S. Pat. No. 5,432,075, or the viral vector's coat protein can be modified so as to decrease the viral vector's ability or inability to be recognized by a neutralizing antibody directed against the wild-type coat protein, as described in PCT International Publication No. WO 98/40509.

Any DNA encoding an angiogenic peptide and operably linked to suitable expression signals can be used within the context of the present invention. Whereas the DNA can be operably linked to any suitable set of expression signals, preferably, the expression of the DNA is under the control of the cytomegalovirus (CMV) immediate early promoter.

Additionally, the DNA can encode any suitable angiogenic peptide. Preferably, the angiogenic peptide is a VEGF protein, and more preferably, the angiogenic peptide is $VEGF_{121}$, $VEGF_{145}$, $VEGF_{165}$, $VEGF_{189}$ or a mammalian counterpart, which are variously described in U.S. Pat. No. 5,332,671 (Ferrara et al.), U.S. Pat. No. 5,240,848 (Keck et al.), and U.S. Pat. No. 5,219,739 (Tischer et al.). Most preferably, because of their higher biological activity, the angiogenic peptide is $VEGF_{121}$ or $VEGF_{165}$, particularly $VEGF_{121}$. A notable difference between $VEGF_{121}$ and $VEGF_{165}$ is that $VEGF_{121}$ does not bind to heparin with a high degree of affinity as does $VEGF_{165}$. Generally, VEGF moieties are advantageous over other angiogenic peptides because VEGF proteins do not induce the growth of tissues not involved in the production of new vasculature. Other angiogenic peptides include VEGF II, VEGF-C, FGF-4, angiogenin, angiogenin-2, and P1GF, which are variously described in U.S. Pat. No. 5,338,840 (Bayne et al.) and U.S. Pat. No. 5,532,343 (Bayne et al.), International Patent Application WO 95/24473 (Hu et al.), European Patent Documents 476 983 (Bayne et al.), 506 477 (Bayne et al.), and 550 296 (Sudo et al.), and Japanese Patent Documents 1038100, 2117698, 2279698, and 3178996.

The adenoviral vector also can include a DNA encoding an angiogenic peptide receptor. Suitable angiogenic peptide receptors include, for example, FLT-1, FLK-1, and FLT-4. Indeed, in certain embodiments, the adenoviral vector can utilize a DNA encoding an angiogenic peptide receptor in place of, rather than in addition to, the DNA encoding an angiogenic peptide.

The DNA, operably linked to expression signals and encoding the angiogenic peptide, can be inserted into any suitable region of the adenoviral vector as an expression cassette. In that respect, the skilled artisan will readily appreciate that there are certain advantages to using an adenoviral vector deficient in some essential gene region of the adenoviral genome inasmuch as such a deficiency will provide room in the vector for a transgene and will prevent the virus from replicating. Preferably, the DNA segment is inserted into the E1 region of the adenoviral vector. Whereas the DNA segment can be inserted as an expression cassette in any suitable orientation in any suitable region of the adenoviral vector, preferably, the orientation of the DNA segment is from right to left. By the expression cassette having an orientation from right to left, it is meant that the direction of transcription of the expression cassette is opposite that of the region of the adenoviral vector into which the expression cassette is inserted.

An adenoviral vector illustrative of the present inventive vector is deficient in the E1a region, part of the E1b region, and part of the E3 region of the adenoviral genome and contains the DNA encoding human $VEGF_{121}$ or human $VEGF_{165}$ under the control of the CMV immediate early promoter in the E1 region of the adenoviral genome. Such a vector supports in vivo expression of VEGF that is maximized at one day following administration and is not detectable above baseline levels as little as one week after administration. This is ideal inasmuch as it is sufficient to provide substantial growth of new vasculature while minimizing adverse neovascularization at distal sites. In that regard, when this vector is locally administered to a target tissue, no detectable VEGF expression can be detected in blood serum using standard ELISA monitoring assays.

Advantageously, local administration to a target tissue of adenoviral vectors encoding human $VEGF_{121}$ or $VEGF_{165}$ in the E1 region of the adenoviral genome are able to increase blood flow at least 3-fold in the extremities of mammals (e.g., the hindlimb of Sprague-Dawley rats) with iliac and femoral artery ligations.

Pharmaceutical Composition

The angiogenic vector desirably is administered to the target tissue in a pharmaceutical composition which comprises a pharmaceutically acceptable carrier and the angiogenic vector.

Any suitable pharmaceutically acceptable carrier can be used within the context of the present invention, and such carriers are well known in the art. The choice of carrier will be determined, in part, by the particular site to which the composition is to be administered and the particular method used to administer the composition. Formulations suitable for injection include aqueous and non-aqueous solutions, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous injection solutions and suspensions can be prepared from sterile powders, granules, and tablets of the kind previously described. Preferably, the pharmaceutically acceptable carrier is a buffered saline solution.

Although any suitable volume of carrier can be utilized within the context of the present invention, preferably, the angiogenic vector is administered in small volumes of carrier so that the tissue to be vascularized (i.e., the target tissue) is perfused with the angiogenic vector but the angiogenic vector is not carried by the blood, lymphatic drainage, or physical mechanisms (e.g., gravitational flow or osmotic flow) to tissues which have not been targeted.

In the case of most applications, particularly to discrete organs such as with respect to human myocardial injections, the volume administered is preferably less than 20 ml (e.g., about 0.1–20 ml) per each administration and more preferably less than about 2.5 ml (e.g., about 0.5–2.5 ml) per each administration.

Dosage

The determination of the proper dosage of the angiogenic vector can be easily made by those of ordinary skill in the art. However, generally, certain factors will impact the dosage which is administered.

Although the proper dosage is such that angiogenesis is induced in the target tissue, preferably, the dosage is sufficient to have a therapeutic and/or prophylactic effect on target tissue which is affected by or at risk of being affected by a vascular occlusion which may lead to ischemic damage of the tissue. Additionally, the dosage should be such that induction of angiogenesis in non-targeted tissue is minimized.

The dosage also will vary depending upon the angiogenic substance to be administered. Specifically, the dosage will vary depending upon the particular vector and DNA, encoding and controlling the expression of the angiogenic peptide in the vector, which are utilized. A dose typically will be at least about $1\times10^6$ pfu (e.g., $1\times10^6$–$1\times10^{13}$ pfu) to the target tissue, e.g., a discrete organ, such as a human heart. The dose preferably is at least about $1\times10^7$ pfu (e.g., about $1\times10^7$–$1\times10^{13}$ pfu), more preferably at least about $1\times10^8$ pfu (e.g., about $1\times10^8$–$1\times10^{11}$ pfu), and most preferably at least about $1\times10^9$ pfu (e.g., about $1\times10^9$–$1\times10^{10}$ pfu). The dose typically is for a volume of targeted tissue of about 100 cm$^3$, more typically about 150 cm$^3$. The dose is administered via multiple applications, and, as such, is divided among the multiple applications. Thus, if the dose is administered via 10 administrations, each administration involves about $1\times10^5$–$1\times10^{12}$ pfu. Preferably, each application involves about $1\times10^6$–$1\times10^{12}$ pfu, more preferably about $1\times10^7$–$1\times10^{10}$ pfu, and most preferably about $1\times10^8$–$1\times10^9$ pfu. For purposes of considering the dose in terms of particle units (pu), also referred to as viral particles, it can be assumed that there are 100 particles/pfu (e.g., $1\times10^{12}$ pfu is equivalent to $1\times10^{14}$ pu). In a single round of vector administration, using, for example, an adenoviral vector deleted of the E1a region, part of the E1b region, and part of the E3 region of the adenoviral genome, wherein the vector carries human $VEGF_{121}$ or $VEGF_{165}$ under the control of a standard CMV immediate early promoter, about $10^7$–$10^{13}$ pfu, preferably about $10^9$–$10^{11}$ pfu, are administered to a targeted tissue (e.g., to a discrete organ containing the targeted tissue) with an estimated volume of about 150 cm$^3$. Under these conditions, a substantial level of VEGF production is achieved in the target tissue without producing detectable levels of VEGF production in distal tissues.

Furthermore, with respect to multiple applications of the angiogenic vector, each application can be such that a dosage gradient is administered across the region defined by the multiple applications. Alternatively, each of the multiple applications can be such that a substantially uniform dose is administered across the region defined by the multiple applications.

EXAMPLES

The following examples further illustrate the present invention but in no way should be construed to limit the scope thereof.

Example 1

This example illustrates the present invention's ability to induce angiogenesis in vivo by administration of a replication-deficient recombinant adenovirus vector (Ad vector). Comprising a DNA encoding an angiogenic (particularly VEGF) peptide.

The replication-deficient recombinant Ad vector containing the DNA for an illustrative angiogenic (particularly VEGF peptide) VEGF$_{165}$, was engineered according to a technique described in *Gastroenterology*, 106, 1638–1644 (1994). The DNA for VEGF$_{165}$, including the signal sequence for secretion, was inserted into an expression plasmid and was under the control of the constitutive CMV immediate-early promoter/enhancer. The expression plasmid also contained the Ad5 sequence from nucleotide 3384 to nucleotide 5778 (9.24 to 16.05 map units), which served as the homologous recombination sequence. The plasmid carrying the DNA for VEGF$_{165}$ was cotransfected with the plasmid pJM17 (from F. Graham, McMaster University, Hamilton, Ontario, Canada) into 293 cells (American Type Culture Collection, CRL1573). The plasmid pJM17 contains the full-length Ad5 DNA (36 kb) and pBRX, a 4.2-kb insert placed in the E1 region, thus exceeding by approximately 2 kb the maximum packaging limit of DNA into the Ad capsid. Homologous recombination between the expression plasmid and pJM17 in 293 cells replaced the E1 region and pBRX insert with the expression cassette from the expression plasmid. The growth of E1 deleted adenoviral vectors is limited to complementary cells, and was carried out in 293 cells, a human embryonic kidney cell line that has been transformed by Ad5 and expresses the E1 region in trans. Culture medium for the 293 cells was improved minimal essential medium with 10% heat-inactivated fetal bovine serum, 2 mmol/L glutamine, 50 U/ml penicillin, and 50 µg/ml streptomycin (all from Biofluids). After cotransfection, individual viral plaques were isolated and amplified in 293 cells. The control vector was AdCMV.βgal, which carries the DNA for the *E. coli* lacZ gene and codes for the enzyme β-galactosidase. AdCMV.VEGF$_{165}$ and AdCMV.βgal were propagated in 293 cells and were purified by CsCl density purification. Subsequently, the preparations were dialyzed and stored in dialysis buffer (10 mmol/l Tris-HCl and 1 mmol/l MgCl$_2$, pH=7.4) with 10% glycerol at −70° C. The titer of each viral stock was determined by plaque assay in 293 cells, and the titers consistently ranged between 5×10$^9$ and 2×10$^{11}$ pfu/ml.

In order to assess the effects of Ad-mediated gene transfer in vivo, either AdCMV.VEGF$_{165}$ or AdCMV.βgal (2×10$^{10}$ pfu) was resuspended in 0.5 ml Matrigel. Subsequently, C57BL mice (Jackson Laboratories, Bar Harbor, Me.) were injected subcutaneously, near the abdominal midline, with the entire 0.5 ml Matrigel containing either AdCMV.VEGF$_{165}$ or AdCMV.βgal. Additional animals were injected with vector-free Matrigel. Mice were studied according to four different protocols.

Protocol 1: To establish whether Ad vectors resuspended in Matrigel infect the surrounding tissues, mice were injected either with Matrigel containing AdCMV.βgal (n=5) or Matrigel alone (n=3). The animals were killed 6 days after injection, and the Matrigel plugs were removed and fixed. Subsequently, the Matrigel plugs were sectioned, stained with X-gal, and examined for evidence of blue staining.

Protocol 2: To establish the duration of transgene expression in vivo, mice were injected either with Matrigel containing AdCMV.VEGF$_{165}$ (n=9), or Matrigel alone (n=9). Animals were killed, and the Matrigel plugs were removed 3, 7, and 21 days after injection. Tissue blocks were immersed in OCT compound (Miles, Inc.) and rapidly frozen in liquid nitrogen. Tissue blocks were stored at −70° C. for less than 1 month. For immunohistochemical evaluation, 10 µm frozen sections (Microm cryotome) were mounted on silanated slides (Digene Diagnostics). Sections were air-dried for 15 minutes, and either stored at −70° C. for up to 48 hours or fixed immediately in 1×Histochoice (Amresco) containing 0.1% Triton X-100 (Sigma Chemical Co.) for 12 minutes. After they were washed with PBS (ph=7.4), slides were incubated in 0.5% hydrogen peroxide in methanol to inhibit endogenous peroxidase activity. Anti-VEGF primary rabbit antibodies were detected by using biotinylated goat anti-rabbit IgG secondary antibody and the avidin-biotin complex and visualized by diaminobenzidine (all detection reagents were from Vector Laboratories). Procedures were performed according to package directions, except sections were kept in blocking solution for at least 45 minutes before the addition of the primary antibody, and incubations with anti-VEGF or control serum (1:6000 dilution) were performed overnight at 4° C. Sections were counterstained in hematoxylin. Anti-VEGF antibodies were produced in rabbits, except the peptide was conjugated to a carrier protein, KLH, by 0.2% glutaraldehyde. Antibodies to KLH alone were also raised and used as a negative control. Antibody specificity was determined by recognizing human VEGF on Western blots, and both anti-KLH and prebleed serum were used as negative controls to determine background staining.

Protocol 3: The presence of newly formed blood vessels was evaluated, as described in *Lab Invest.*, 67, 519–528 (1992), in mice killed 14 days after the injection of the Matrigel (n=8 mice for each Ad vector; 4 mice were used in each of two separate experiments). The gels were recovered by dissection and fixed. Histological sections were stained with Masson's trichrome stain and evaluated for the presence of neovascularization. The thickness of the stroma surrounding the Matrigel was assessed by measuring the distance between the surface of the Matrigel and the abdominal muscle in two different histological sections from each plug. Ten measurements were obtained at 50 to 100 µm intervals from each histological section, and the 20 measurements from the two sections were averaged to express stromal thickness for each individual plug.

Protocol 4: The angiogenic response was quantified by the hemoglobin content of the Matrigel plugs (n=10 mice for each Ad vector; 3 or 4 mice were used in each of three separate experiments).

With respect to the experiments conducted to establish whether Ad vectors resuspended in Matrigel could diffuse out of the gel and infect the surrounding tissue, mice were killed 6 days after injection of Matrigel containing AdCMV.βgal or Matrigel alone, and the Matrigel plugs were stained with X-gal. X-gal positive cells were found in the stroma surrounding the Matrigel. In contrast, no blue cells were found in the tissue surrounding uninfected gel plugs. In other experiments, the duration of Ad-mediated $VEGF_{165}$ gene expression in vivo was established. By immunohistochemical staining, plugs recovered 3 days after coinjection of Matrigel and $AdCMV.VEGF_{165}$ showed VEGF-positive cells in the tissue surrounding the Matrigel. Staining was most intense at day 7, and only a few cells were immunoreactive 21 days after injection. Incubations in the absence of the primary antibody showed no immunostaining. Incubations with the antibody against the carrier protein showed positivity in the abdominal muscle layer; however, no positivity was found in the tissue surrounding the Matrigel plugs. The Matrigel plugs were examined histologically 14 days after injection, and angiogenesis was observed in the tissues surrounding the Matrigel in response to $AdCMV.VEGF_{165}$. This effect was associated with increased vascularity and thickening of the stromal matrix surrounding the Matrigel. In contrast, AdCMV.βgal resulted in some thickening of the stromal matrix surrounding the Matrigel without evidence of increased vascularization, and Matrigel alone was not associated with increased stromal thickening or angiogenesis. Furthermore, the quantitative assessment of angiogenesis demonstrated that the hemoglobin content of the Matrigel plugs with $AdCMV.VEGF_{165}$ was four-fold higher than in the case of the gel explants with AdCMV.βgal. A significant increase in hemoglobin content also was observed with AdCMV.βgal-infected versus uninfected control plugs. Together, these results show that an adenoviral vector comprising a DNA encoding an angiogenic (particularly VEGF) peptide induces angiogenesis in vivo.

Example 2

This example illustrates the present invention's ability to direct in vivo gene transfer to myocardium using a replication-deficient adenovirus vector.

A replication-deficient vector, AdCMV.VEGF, was an E1a⁻, partial E1b⁻, partial E3⁻ adenovirus vector that contained an expression cassette in the E1 position which contained the cytomegalovirus immediate early promoter/enhancer (CMV) driving the DNA for human $VEGF_{165}$. AdCMV.Null (similar to AdCMV.VEGF, but with no gene in the expression cassette) was used as a control vector for in vitro experiments. AdCMV.CAT (similar to AdCMV.VEGF, but coding for chloramphenicol acetyl transferase) was used to transfer and express a marker gene. All adenovirus vectors were propagated in 293 cells, purified by CsCl density purification, dialyzed, and titered by plaque assay. Vectors were stored in 50 μl aliquots at −70° C.

Male mongrel dogs (25 to 30 kg) were used for all the studies. Anesthesia was induced with intravenous methohexital (Brevital; Eli Lilly, Indianapolis, Ind.; 10 mg/kg), and after intubation, anesthesia was maintained using inhaled isoflurane (1–2% in 2–3 $O_2$). For direct myocardial injections, a left lateral thoracotomy was performed under sterile conditions. The pericardium was divided anterior to the phrenic nerve, and three separate marking sutures (5-0 monofilament) were placed at 3.5 cm intervals along the left ventricular free wall. Adenovirus vectors were administered at marked locations in a volume of 100 μl using a 0.5 ml syringe with a 30 gauge needle. The needle tip was positioned at a depth of 3 to 5 mm from the epicardial surface, and satisfactory delivery was confirmed visually. The pericardium and chest were closed in a standard fashion, and the animals were permitted to recover.

To evaluate the feasibility of achieving sustained local levels of a therapeutic angiogenic protein in myocardium, AdCMV.VEGF ($10^9$ pfu) was administered by direct myocardial injection (two injections per animal; 12 animals). Tissue samples (1 cm³) from the site of vector administration were harvested and evaluated for VEGF expression immediately and at 2, 5, 7, and 14 days after vector administration. Tissue injected with the AdCMV.CAT vector was used as a negative control.

Quantification of VEGF expression in myocardium was performed with the Quantikine human VEGF immunoassay (R&D Systems, Inc., Minneapolis, Minn.). Tissue samples (0.5 g) from the sites of vector administration were homogenized with protein lysis buffer (10 mmol/l Tris-HCl, pH=8, 0.14 mol/l NaCl, 0.025% $NaN_3$, 2% Triton X-100, and 1 mmol/l phenylmethylsulfonyl fluoride; 2 ml/g tissue), protein determinations were performed, aliquots of protein lysate (100 μg) were analyzed in triplicate, and absorbance was measured at 450 nm using a microplate reader. The concentration of VEGF was normalized to mg protein. The spatial limit of VEGF expression was determined by evaluation of tissue samples from animals sacrificed at 7 days. Tissue was divided into central, peripheral, epicardial, and endocardial components, and each sample was evaluated individually for VEGF expression.

To determine whether localized expression of VEGF would result in detectable levels of VEGF in the serum, blood samples were obtained from the animals before vector administration and at the times of sacrifice at 2, 5, 7, and 14 days after vector administration. Quantification of VEGF was performed by enzyme-linked immunosorbent assay on 50 μl samples of serum.

To evaluate the systemic effect of direct myocardial injections of adenoviral vectors in the myocardium, serum biochemistry and complete blood count indices were monitored over time. Blood samples for white blood cell count, hematocrit, platelet count, alkaline phosphatase, serum glutamic-pyruvic transaminase, bilirubin, and creatinine were obtained from the animals before vector administration and at 2, 7, and 14 days after vector administration. Values for each time were averaged. Serum chemistry determinations were calculated with the Du Pont Analyst Benchtop Chemistry System (Du Pont Co., Wilmington, Del.), and complete blood count determinations were made with the System 900 Hematology Analyzer (Serono Diagnostics, Allentown, Pa.).

To determine the effect of direct myocardial gene transfer on cardiac function, transthoracic two-dimensional Doppler and echocardiograms using a Hewlett-Packard 2500 echocardiographic machine (Hewlett-Packard Co., Andover, Mass.) and a 3.5-MHz transducer were performed. The following images were obtained preoperatively and either 5 to 7 days postoperatively or 14 days postoperatively: the parasternal long-axis view, the parasternal short-axis view at the tip of the papillary muscles, and the apical five-chamber view. Pulsed-wave Doppler echocardiography at the level of the aortic annulus was also performed from the apical five-chamber view.

Off-line analysis of regional wall thickening was performed by tracing the endocardial and epicardial surfaces of the left ventricle in both diastole and systole. The ventricle was then divided into six equal radial segments, with segment 1 beginning at the inferior ventricular septum and subsequent segments labeled consecutively in a clockwise fashion, with segment 6 ending at the inferior wall. Segments 3 and 4, therefore, represent the anterolateral free wall of the left ventricle. The mean wall thickness of each segment was determined. Systolic wall thickening in each segment was defined as the mean systolic wall thickness minus the mean diastolic wall thickness. As an assessment of global left ventricular function, cardiac output was calculated using standard Doppler-derived stroke volume (aortic annular area times the velocity time integral of the flow velocity profile across the aortic annulus) and the recorded heart rate.

Confirmation of VEGF protein expression in vivo after direct myocardial administration of AdCMV.VEGF was achieved by enzyme-linked immunosorbent assay. Quantification of VEGF expression in myocardium over time demonstrated that administration of AdCMV.VEGF resulted in a more than 18-fold increase over baseline VEGF expression 2 days after vector administration and a more than 15-fold increase over baseline 7 days after vector administration. By day 14, VEGF levels had returned to baseline. In contrast, administration of the control vector AdCMV.CAT did not result in significantly increased levels of VEGF expression over baseline at any of the times examined. The levels of VEGF on day 0, obtained immediately after vector administration, were similar to levels in the naïve tissue, confirming that the viral preparation was not contaminated with VEGF protein. Furthermore, in support of the concept that adenovirus vector delivery provides a localized gene transfer strategy, no levels of VEGF could be detected in the serum of treated animals at any of the times examined.

Consistent with the data obtained with marker gene transfer, the administration of AdCMV.VEGF was also characterized by a wide spatial limit of gene expression. In contrast to the results obtained for AdCMV.CAT, however, 7 days after administration of AdCMV.VEGF, levels of VEGF expression were equally increased in all four spatial regions (central and peripheral epicardium and central and peripheral endocardium) up to 15 mm from the site of vector administration, suggesting a homogeneous distribution of protein through all tissue samples.

All animals that received adenovirus vectors survived to their predetermined times for sacrifice. No animals demonstrated failure to thrive or tachycardia or were febrile, and no wound infections developed. There were no significant changes over baseline in white blood cell count, hematocrit, platelet count, alkaline phosphatase, serum glutamic-pyruvic transaminase, bilirubin, or creatinine in the animals examined at 2, 7, and 14 days after vector administration.

Echocardiograms performed on the animals before vector administration and 5 to 7 days or 14 days after administration demonstrated no significant change in global or regional ventricular function. Regional wall motion assessment revealed no significant difference in the systolic wall thickening of any of the six radial segments between the preoperative and postoperative studies. Cardiac output also did not change significantly between the preoperative and postoperative studies.

In summary, it has been shown that a wide spatial limit of gene expression has been characterized after adenovirus-mediated direct myocardial gene transfer, and the delivery system has been shown to be safe and well tolerated. Furthermore, using a large animal model with physiology similar to that of a human, it has been shown that an in vivo administration of an adenovirus vector encoding a therapeutic angiogenic protein (particularly VEGF) resulted in sustained and localized protein expression for a number of days after gene transfer.

Example 3

This example illustrates the present invention's ability to protect against threatened ischemic vascular occlusions by inducing salvage angiogenesis via adenoviral-mediated gene transfer of an angiogenic peptide (particularly VEGF).

A model of acute vascular occlusion superimposed upon pre-existing ischemia was created using male Sprague-Dawley rats weighing 250 to 300 g. Animals were anesthetized with intramuscular ketamine (100 mg/kg) and xylazine (2 mg/kg), a midline laparotomy was performed under sterile conditions, and the left common iliac artery was ligated and divided. The adenoviral vectors were then administered in the left iliofemoral adipose tissue and muscle, and the abdomen was closed in two layers with non-absorbable suture. AdVEGF (total dose=$4\times10^9$ pfu), the control vector AdNull (total dose=$4\times10^9$ pfu), or PBS (total dose=$4\times100$ $\mu$l) at the time of iliac artery ligation was administered in a volume of 100 $\mu$l at each of four sites using a 0.5 ml syringe with a 30-gauge needle. In the region targeted for collateral vessel formation, 4 individual vector administrations were performed at consistent locations in the left iliofemoral region of each animal, including retroperitoneal and inguinal adipose tissue, psoas muscle, and quadriceps muscle. An additional group of control animals underwent unilateral common iliac ligation alone with no treatment.

Three weeks following left common iliac ligation and vector administration, animals were anesthetized as described above, and the left common femoral artery was ligated and divided at the level of the inguinal ligament. Immediate analysis of relative hindlimb blood flow and vascularity were then conducted utilizing, in the following order: (1) $^{99m}$Tc-labeled sestamibi; (2) color microspheres; (3) angiography; and (4) histologic quantification of blood vessel number.

The replication-deficient vector AdVEGF was an E1a$^-$, partial E1b$^-$, partial E3$^-$ adenoviral vector that contained an expression cassette in the E1 position containing the cytomegalovirus immediate early promoter/enhancer (CMV) driving the DNA for the 165 residue form of human VEGE (VEGF$_{165}$). AdNull (similar to AdVEGF, but with no gene in the expression cassette) was used as a control vector. All adenoviral vectors were propagated in 293 cells, purified by CsCl density purification, dialyzed, and stored at $-70°$ C. The titer of each viral stock was determined by plaque assay in 293 cells. All viral stocks were demonstrated to be free of replication-competent wild-type adenovirus.

To confirm that the AdVEGF vector could mediate transfer and expression of the VEGF DNA to adipose tissue and skeletal muscle, an enzyme-linked immunoassay (ELISA) was used to quantify VEGF levels in tissue recovered from animals 0, 1, 3, 5, and 7 days following common iliac ligation and vector administration ($10^9$ pfu/site; n=3 each time point). Retroperitoneal adipose tissue and quadriceps muscle of animals treated with the vectors were harvested, rinsed in phosphate-buffered saline, pH=7.4 (PBS), and homogenized with protein lysis buffer [10 mM Tris-HCl pH=8, 0.14 M NaCl, 0.025% NaN$_3$, 2% Triton X-100, and 1 mM phenylmethylsulfonyl fluoride (2 ml/g tissue)]. To confirm that the VEGF produced remained localized, serum was obtained from each animal at the above time points. Protein determinations were performed using the Bradford method, and ELISA for VEGF was carried out [Quantikine human VEGF Immunoassay, R&D Systems, Minneapolis, Minn.] using 50 $\mu$g tissue (each assay carried out in duplicate for each animal). Absorbance was measured at 450 nm using a microplate reader, and VEGF concentration was normalized to mg protein.

$^{99m}$Tc-labeled sestamibi scanning was used as a measure of blood flow to the hindlimb. To accomplish this, the right jugular vein was identified through a limited right cervical incision, and 2–3 mCi of $^{99m}$Tc-labeled sestamibi (Cardiolite, Dupont Pharma, North Billerica, Md.) in a volume of 0.5 ml of PBS (0.9%) was injected intravenously. Approximately 15 min after the injection, animals were placed in the supine position on the lower detector of an ADAC Vertex dual head gamma camera system (ADAC Laboratories, Milpitas, Calif.), and ventral and dorsal whole-body gamma camera images were acquired using low-energy high-resolution parallel-hole collimators and a photopeak energy window of 140 keV±10%. At least 2×10$^5$ counts per animal were acquired simultaneously from the dorsal (lower detector) and ventral (upper detector) images. Pegasys™ computer and image processing software (ADAC Laboratories) were used to manually draw consistent rectangular regions of interest (ROI) over the center of the calves of the left and right hindlimbs by an individual blinded to the treatment groups, and the mean counts per pixel in these regions were determined. Relative blood flow was reported as the ratio of the ROI mean counts per pixel in the ligated (left) hindlimb to the ROI mean counts per pixel in the contralateral (right) control hindlimb for the geometric mean of ventral and dorsal images.

Blood flow to the ischemic (left) hindlimb relative to the normal (right) hindlimb also was evaluated by intraarterial administration of 15 $\mu$m color microspheres as an assessment of functional blood vessels to the limb. The abdominal aorta was identified through a midline laparotomy, and loosely encircled with a 4–0 silk suture. Immediately distal to the suture, a 24-gauge, ¾-inch (1.9 cm) Angiocath (Becton Dickinson Vascular Access, Sandy, Utah) was inserted into the infrarenal aorta, and 0.5 ml of a solution of nitroglycerin [Abbott Laboratories, North Chicago, Ill. (500 $\mu$g/ml)] and 2×10$^6$ of 15 $\mu$m color microspheres [E-Z Trac, Los Angeles, Calif. (2×10$^6$ microspheres in 200 $\mu$l)] were vortexed and injected through the catheter over 20 seconds to ensure adequate mixing of the microspheres. At sacrifice, all lower hindlimb calf musculature was dissected free from skin and bone, weighed, digested with Tissue Digest Reagents 1 and 2 (E-Z Trac) according to manufacturer's instructions, and resuspended in 50 $\mu$l Microsphere Counting Reagent (E-Z Trac). Microspheres were counted by an individual blinded to treatment groups using a manual hemocytometer, with a minimum of 400 spheres counted per sample. The number of microspheres per gram of tissue was determined, and relative blood flow was reported as microspheres/gm (wet weight) tissue in the ligated hindlimb versus microspheres/gm of wet tissue in the contralateral control hindlimb.

Angiography was used as an assessment of macroscopic vascularity. To do this, animals were positioned supine, at a distance of 20 cm from the collimator of a Mobile Surgical X-ray System BV25 (Philips, Holland). Using a 24 gauge, ¾-inch (1.9 cm) angiocatheter (Becton Dickinson, Sandy, Utah) placed into the infrarenal aorta, 0.5 ml nitroglycerin (500 $\mu$g/ml; Abbott Laboratories) was injected over 20 seconds. Immediately thereafter, 3 ml of Renografffin-76 (Squibb Diagnostics, New Brunswick, N.J.) were injected through the catheter into the distal aorta, and fluoroscopic images were obtained at 2 second intervals. Representative images demonstrating maximal arterial opacification were developed, and vascularity was scored by three observers in a blinded fashion. A vascular score was determined for each animal by drawing a line perpendicular to the midpoint of the long axis of the femur; the number of vessels crossing this line were counted by each observer, averaged, and reported as a "vascular score."

Histologic evaluation was used to quantify vascularity at the small vessel level at the sites receiving the adenoviral vectors. For the treated adipose tissue sites, 1 cm$^3$ adipose tissue samples from sites of vector administration were retrieved, rinsed in PBS and stored in 4% formalin at 4° C. Samples were embedded in paraffin, serial 5 $\mu$m cross-sections in a plane parallel to the surface of the tissue were obtained at intervals of 50 $\mu$m, and immunohistochemical staining for $\alpha$-actin, an endothelial cell specific antigen, was performed. Paraffin sections were blocked with 1.5% horse serum for 20 minutes to prevent non-specific binding, and then exposed to primary antibody (monoclonal anti-human $\alpha$-actin; Sigma, St. Louis, Mo.) at a dilution of 1/500 for 60 minutes. The slides were exposed sequentially (30 minutes each) to biotinylated horse anti-mouse IgG, ABC reagents (Vector Laboratories, Burlingame, Colo.), new fuchsin substrate for alkaline phosphatase (Dako Corp., Carpenteria, Calif.), and then counterstained with hematoxylin. Sections were examined in a blinded fashion by 3 observers at a magnification of 100×. Five random fields of vessels less than 80 $\mu$m were counted per slide; 6 slides were evaluated per sample. The counts were averaged and reported as number of blood vessels per mm$^2$.

To quantify vascularity in treated regions of skeletal muscle, 1 cm$^3$ sections of quadriceps muscle from sites of vector administration were retrieved, rinsed in PBS and then fixed in increasing concentrations of a sucrose phosphate solution (25° C., 1 hour). The skeletal=muscle specimens were then frozen in a 2:1 20% sucrose/OCT (Tissue Tek, Sakura Finetek, Torrance, Calif.) compound mixture at −70° C. The frozen specimens were then cut into 5 $\mu$m sections and frozen on the slides at −70° C. The frozen slides were warmed to room temperature, stained for alkaline phosphatase (25° C., 1 hour) using an insoluble alkaline phosphatase substrate-5-bromo-4-chloro-3-indolyl phosphate, nitro blue tetrazolium (BCIP/NBT tablets, Sigma, St. Louis, Mo.) and counterstained with eosin. Sections were examined at a magnification of 400× in a blinded fashion by 3 observers. Capillaries per muscle fiber were quantified by counting 6 random muscle fibers per field, 5 random fields per slide and 5 slides per animal. The counts were averaged and reported as number of capillaries per muscle fiber.

Successful AdVEGF-mediated gene transfer and expression in adipose and skeletal muscle was confirmed by ELISA. There was no detectable VEGF in either tissue on day 0 (obtained immediately following vector administration), similar to naïve adipose tissue and skeletal muscle, confirming that the vector preparation was not contaminated with VEGF protein. For both tissues, quantification of VEGF expression demonstrated that administration of AdVEGF resulted in VEGF expression, peaking 1 day following vector administration, and decreasing over several days to baseline by 1 week following vector administration. In contrast, administration of the control vector AdNull resulted in no detectable VEGF expression in either tissue at any timepoint. Importantly, consistent with the concept that the adenoviral vector delivery provides a localized gene transfer and expression strategy, no VEGF could be detected in the serum of AdVEGF-treated animals at any of the timepoints after vector delivery, and administration of AdNull did not result in increased serum levels of VEGF over baseline. Endogenous VEGF could not be detected in serum or in the tissues as the ELISA used for these experiments detects human VEGF only and not rat VEGF.

$^{99m}$Tc-labeled sestamibi imaging demonstrated a significantly greater relative blood flow to the ischemic hindlimb in animals treated with AdVEGF. The scanned radioactive images of AdNull-treated control animals demonstrated low level of radioactivity in the calf region of the ligated hindlimb. Naïve and PBS-treated control animals had similar low levels of radioactivity in this region, as did naïve and AdNull controls. Although both the AdNull and PBS controls had low levels of radioactivity in the calf region, the AdNull group was slightly higher than the PBS group.

Color microsphere analysis demonstrated that the relative blood flow following femoral artery ligation in AdVEGF-treated animals was nearly 3-fold greater than that observed in any of the control animals [AdNull-treated, PBS-treated or naïve animals]. Relative blood flow in naïve and PBS-treated controls was similar to that for AdNull-treated animals. The increase in the relative blood flow in AdVEGF-treated animals compared to controls, calculated as the ratio of microspheres/gm tissue in the ligated hindlimb versus microspheres/gm tissue in the contralateral control hindlimb, resulted from an increase in the number of microspheres in the ligated hindlimb, not a decrease in the number of spheres in the contralateral control hindlimb. To confirm that there was adequate mixing of color microspheres during injection, relative blood flow to each hindlimb was quantified in a separate group of animals without undergoing any iliac or femoral ligation (n=6). Relative blood flow (left versus right) in these animals was 99%±7%.

Angiography demonstrated significantly greater vascularity in the ligated hindlimb in AdVEGF-treated animals than in controls, with collateral formation that partially reconstituted the distal hindlimb vasculature. The angiographic vessel score in the ligated hindlimb of AdVEGF-treated animals was significantly greater than that of naïve, PBS-treated and AdNull treated controls. The number of angiographically visible collateral vessels in the naïve and PBS-treated animals were similar, as were the number of vessels in the PBS and AdNull treated animals. The number of vessels in the naïve control were greater than that in the AdNull group, but both were less than the AdVEGF group.

Histologic evaluation of vascularity in adipose tissue and skeletal muscle was consistent with the observations made of relative blood flow and angiographic evidence of enhanced vascularity. Compared to the naïve, PBS-treated and AdNull-treated controls, a significantly greater number of small blood vessels were observed 21 days following vector administration in the AdVEGF injected adipose tissue. Quantitative assessment of the histologic samples of AdVEGF-treated adipose tissue resulted in a 52%±6% increase in small vessel number when compared to the naïve, PBS and AdNull controls. Similarly, histologic evaluation of AdVEGF-treated quadriceps skeletal muscle demonstrated a significantly greater number of capillaries per muscle fiber 21 days following vector administration compared to the naïve, PBS-treated and the AdNull-treated controls. Quantitative assessment of AdVEGF-treated skeletal muscle demonstrated a significant increase in mean capillary numbers per muscle fiber compared to naïve, PBS-treated and AdNull-treated controls.

The results demonstrate that adenoviral-mediated transfer of the DNA of human $VEGF_{165}$ in vivo to adipose and skeletal muscle tissues surrounding and distal to a site of vascular occlusion induces an angiogenic response adequate to attenuate the ischemia caused by subsequent acute vascular occlusion. Also, the results indicate that not only can angiogenic mediators be used to enhance angiogenic responses following an acute ischemic event, but they also can be used to "salvage" ischemic tissues threatened by subsequent acute vascular occlusion. The demonstration of enhanced blood flow to protect ischemic tissues weeks after the expressed angiogenic protein is no longer detectable illustrates that administration of an adenoviral vector comprising a DNA which encodes an angiogenic peptide is sufficient to provide a physiologically significant angiogenic response.

Example 4

This example illustrates the present invention's ability to improve myocardial perfusion and function in ischemic heart via adenoviral-mediated gene transfer of a DNA encoding an angiogenic peptide (particularly $VEGF_{121}$).

A model of chronic myocardial ischemia was created in Yorkshire swine weighing 28 to 30 kg. Animals were sedated with intramuscular tiletamine and zolazepam (Telazol, 3.3 mg/kg) and xylazine (0.10 mg/kg) and then intubated, and sedation was maintained with 0.5% to 2.0% isoflurane. A limited left thoracotomy was performed in a sterile fashion through the fifth intercostal space, and a small incision was made in the pericardium. A 2.5 mm internal diameter ameroid constrictor (Research Instruments & MFG, Corvallis, Oreg.) was placed around the circumflex artery as proximally as possible. Topical lidocaine 1% solution was applied to the circumflex artery at the ameroid constrictor site to prevent coronary artery spasm. The pericardium and chest were then closed, and the animal was allowed to recover.

The replication-deficient vector $AdVEGF_{121}$ is an $E1a^-$, partial $E1b^-$, partial $E3^-$ adenoviral vector that contains an expression cassette in the E1 position (right to left) containing the cytomegalovirus (CMV) immediate early promoter/enhancer, an artificial splice sequence, the human $VEGF_{121}$ DNA, and the SV40 polyA/stop signal. AdNuli (similar to $AdVEGF_{121}$, but with no gene in the expression cassette) was used as a control vector. All adenoviral vectors were propagated and titrated in 293 cells, purified by cesium chloride density purification, dialyzed, and stored at $-70°$ C. The viral stocks were demonstrated to be free of replication-competent wild-type adenoviruses. Biologic activity of the $VEGF_{121}$ transgene product was confirmed by demonstrating proliferation of human umbilical vein endothelial cells using [$^3$H]thymidine incorporation, and in vivo confirmation of transgene expression was determined by enzyme-linked immunosorbent assay analysis of myocardial biopsy specimens obtained from $AdVEGF_{121}$ injection sites 3 days after vector administration.

Three weeks after ameroid constrictor placement, the left thoracotomy was reopened, and administration of the therapeutic vector, $AdVEGE_{121}$, or the control vector, AdNull, was performed by direct myocardial injection. Each vector was injected at 10 sites, each in 100 µl phosphate-buffered saline solution, pH=7.4, in the circumflex distribution ($10^8$ pfu/injection). Pacing wires were placed in the left atrial appendage and tunneled subcutaneously for subsequent stress $^{99m}$Tc-labeled sestamibi assessment of regional myocardial perfusion by single photon emission computed tomography (SPECT) and echocardiographic assessment of regional wall thickening.

Regional myocardial perfusion was evaluated during rest and stress 3 weeks and 7 weeks after placement of the ameroid constrictor by means of $^{99m}$Tc-sestamibi SPECT. During rapid atrial pacing at 200 beats/minute, animals received intravenous injections of a 5 mCi bolus of $^{99m}$Tc-sestamibi, and pacing was continued for approximately 3 minutes. The animals were then placed in the prone position in an ADAC Vertex dual detector gamma camera system (ADAC Laboratories, Milpitas, Calif.). A nongated SPECT study was then acquired in a "step-and-shoot" mode over a 180-degree body-contouring orbit. The animal was allowed to return to baseline heart rate and then received an injection of a 25 mCi bolus of $^{99m}$Tc-sestamibi before obtaining a rest SPECT, acquired in an analogous fashion.

The rest and stress SPECT studies were processed in a blinded fashion with the use of an integrated ADAC Pegasys computer. Stress and rest circumferential count profiles (polar plots) at the midventricular level were constructed by dividing the midventricular short-axis image into 60 angular segments centered on the ventricular cavity, determining the number of counts per segment, normalizing the number of counts in each segment to the segment with the maximum number of counts (assigned a reference value of 100), and plotting the normalized counts per segment versus the angular position of the segment. The polar plots were transferred to ASCII files for further analysis with the program SIGMAPLOT (Jandel Scientific, Corte Madera, Calif.).

For each animal, the extent of myocardial ischemia ("area") was determined from the difference between the rest and stress polar plots. The maximum severity of ischemia ("ischemia maximum") in the circumflex distribution was determined by ascertaining the point of greatest difference between the rest and stress plots and measuring the difference in the plots at that point. The percent improvement in myocardial perfusion for each animal was calculated for these two parameters as ("parameter" at 3 weeks–"parameter" at 7 weeks×100)/("parameter" at 3 weeks).

Baseline regional myocardial function was assessed by echocardiography at rest and during stress at the time of vector administration. Animals were sedated and placed in the left lateral decubitus position, and standard two-dimensional and M-mode transthoracic images were obtained with an HP2500 echocardiographic machine and a 3.0/3.5 MHz dual-frequency transthoracic transducer (Hewlett-Packard, Andover, Mass.). From the right parasternal approach, short-axis, midpapillary views were obtained at rest for 3 minutes. The animals then underwent rapid left atrial pacing in a stepwise fashion to the target ventricular rate of 200 beats/min, at which time imaging was recorded for an additional 3 minutes.

Regional wall thickening was determined by a single experienced investigator in a blinded fashion, tracing the endocardial and epicardial surfaces of the left ventricle in both diastole and systole using a Digisonics CardioRevue System (Digisonics Inc, Houston, Tex.). Systolic wall thickening in each of six equal radial 60-degree segments was defined as mean systolic wall thickness minus mean diastolic wall thickness. Fractional wall thickening was calculated as mean systolic wall thickening divided by mean diastolic wall thickness. The ischemic and nonischemic zones for each animal were defined from rapid atrial pacing images at 3 weeks (baseline ischemia) as the two contiguous segments with the lowest and highest fractional wall thickening, respectively. This corresponded in all cases with the circumflex region and the septum, respectively. The same zones for each animal were analyzed in rapid atrial pacing images at 7 weeks.

When each animal was put to death (4 weeks after vector administration), the heart was arrested with 40 mEq of KCl and then perfusion-fixed at 100 mm Hg with 1 l of McDowell-Trump fixative (4% formaldehyde, 1% glutaraldehyde, 1% $NaH_2PO_4$ and 0.3% NaOH adjusted to pH=7.2). Ex vivo coronary angiography was performed by the same angiographer in a blinded fashion using a 5F end-hole wedge balloon catheter (Arrow Inc., Reading, Pa.) placed in the left main coronary artery. By means of cinefluoroscopy in the standard right anterior oblique projection with continuous image acquisition, 5 ml of contrast medium (Hypaque-76, Nycomed Inc., New York, N.Y.) was injected at a continuous rate until the entire left anterior descending coronary artery and its branches were completely opacified. Collateral vessels from the left anterior descending coronary artery, which reconstituted the circumflex coronary artery or obtuse marginal branch of the circumflex coronary artery, were quantified by three blinded observers using the grading method of Rentrop and associates, as described in *J. Am. Coll. Cardiol.*, 5, 587–592 (1985), as follows: 0=no filling of collateral vessels; 1=filling of collateral branches of the circumflex or obtuse marginal branch without visualization of the epicardial segment; 2 and 3=partial or complete filling of the epicardial segment of the circumflex or obtuse marginal artery via collateral vessels, respectively.

After angiography, the left ventricle of each heart was sectioned into three rings in the short axis. Forty 5 μm histologic sections from each heart were taken at equidistant intervals around the basal and midventricular rings, processed though paraffin, and stained with hematoxylin and eosin. Histologic evidence of infarction and inflammation for each tissue section was graded by a pathologist blinded to treatment on a scale of 0 to 4 as follows: 0=none; 1 one to three small areas involved; 2=less than 10% section surface; 3=more than 10% and up to 50% section surface; and 4=more than 50% section surface.

All of the 19 animals studied ($AdVEGF_{121}$, n=9; AdNull, n=10) survived until put to death 7 weeks after placement of the ameroid constrictor, without clinical evidence of toxicity. At 3 weeks (i.e., before therapy), four of the 19 pigs ($AdVEGF_{121}$, n=2; AdNull, n=2) had evidence of myocardial infarction in the circumflex region, as demonstrated by (1) a fixed defect (no difference between rest and stress) in the circumflex zone of the $^{99m}$Tc-sestamibi SPECT images and (2) a thinned, akinetic posterolateral region of the left ventricle in short-axis views during echocardiography at rest. Consistent with the $^{99m}$Tc-sestamibi SPECT and echocardiography suggesting myocardial infarction 3 weeks after ameroid constrictor placement, the gross pathologic evaluation 4 weeks later showed myocardial scarring and thinning of at least 25% of the total ventricular mass. All four pigs in this subgroup also had histologic evidence of large transmural infarction. On the basis of these data, these four animals were excluded from further analysis. Thus the group of animals evaluated for efficacy of therapy included seven $AdVEGF_{121}$-treated animals and eight AdNull (control) animals.

In vivo expression of the $AdVEGF_{121}$ vector was confirmed by demonstrating local myocardial VEGF expression after myocardial injection of $10^8$ pfu of $AdVEGF_{121}$ (n=3). Three days after administration of the vector, myocardial level were 0.75±0.25 ng/mg protein.

Circumferential count profiles (polar plots) of $^{99m}$Tc-sestamibi SPECT data from the midventricular level were used to quantify (1) the extent and severity of ischemia ("area") and (2) the most severe ischemia ("ischemia maximum"). Circumferential plots of rest images obtained at 3 weeks typically demonstrated minimal perfusion defects, compared with plots of stress (pacing) images, which revealed decreased perfusion in the posterolateral region, corresponding to the occluded circumflex coronary artery distribution. The ischemic area and ischemia maximum were characteristically unchanged from baseline in AdNull animals assessed 4 weeks after vector administration. In contrast, AdVEGF$_{121}$ animals demonstrated improvement in myocardial perfusion 4 weeks after vector administration, as demonstrated by decreases in the ischemic area and ischemic maximum compared with baseline. Corresponding changes were noted at the apical, midventricular, and basal levels.

The ischemic area was similar in both the AdVEGF$_{121}$ and AdNull control animals at the time of vector administration. In contrast, the ischemic area was significantly reduced at 7 weeks in the AdVEGF$_{121}$ animals compared with the AdNull animals. The "percent improvement" in the area of ischemia of each animal 4 weeks after vector administration, compared with baseline, was approximately 2.4-fold greater in the AdVEGF$_{121}$ animals than in the AdNull animals (75%±6% versus 32%±11%, respectively).

The ischemia maximum in the circumflex distribution was also the same for the AdVEGF$_{121}$ and AdNull control animals at 3 weeks. In contrast, 4 weeks after vector administration, the ischemia maximum was significantly decreased in the AdVEGF$_{121}$ animals than in the AdNull control animals. Similarly, the "percent improvement" in the ischemia maximum was 2.5-fold greater in AdVEGF$_{121}$ animals than in the AdNull control animals (56%±8% versus 22%±6%).

Three weeks after ameroid constrictor placement, myocardial function in the ischemic circumflex region compared with the nonischemic septum was similar in the AdVEGF$_{121}$ group compared with AdNull controls as assessed by fractional wall thickening during rapid atrial pacing. In contrast, by 4 weeks after vector administration, AdVEGF$_{121}$ treated animals demonstrated significantly greater improvement in fractional wall thickening during rapid atrial pacing than did AdNull control animals. Strikingly, contractile function in the circumflex segment of the AdVEGF$_{121}$ group approximated that of the septal (control) segment, as reflected by an ischemic minus nonischemic zone difference of "zero" in this analysis.

Ex vivo angiography performed 4 weeks after vector administration confirmed complete occlusion of the proximal circumflex coronary artery by the ameroid constrictor in all animals. AdNull treated animals characteristically demonstrated only partial filling of the obtuse marginal and circumflex coronary arteries. In contrast, animals that received AdVEGF$_{121}$ typically demonstrated nearly complete reconstitution of both the obtuse marginal and circumflex coronary circulations.

The collateral grade for the obtuse marginal and circumflex coronary arteries was significantly greater in the AdVEGF$_{121}$ animals than in the AdNull animals. Finally, the total number of angiographically visible collateral vessels filling the circumflex and obtuse marginal arteries was significantly greater in the AdVEGF$_{121}$ animals than in the AdNull animals.

The myocardium in 13 of the 15 animals in the study was available for assessment of inflammation (AdVEGF$_{121}$, n=5; AdNull, n=8). Minimal inflammation was detected in the myocardium of these animals evaluated 4 weeks after therapy, with no difference in the extent of inflammation between the AdVEGF$_{121}$ and AdNull groups (overall intensity score 0.3±0.06 versus 0.4±0.08).

The results indicate that adenoviral-mediated transfer of the DNA of human VEGF, specifically VEGF$_{121}$ directly into the myocardium of a mammal, as demonstrated with Yorkshire swine, with an occluded circumflex coronary artery results in significant and physiologically relevant improvement in regional myocardial perfusion and contractile function during stress-induced myocardial ischemia. Importantly, this improvement was associated with increased myocardial collateral vessel development, "biologically bypassing" the experimentally occluded coronary artery segment.

Example 5

This example illustrates the present invention's ability to administer AdVEGF$_{121.10}$ to the cardiac tissue of a human.

The replication-deficient vector AdVEGF$_{121.10}$ is an E1a$^-$, partial E1b$^-$, E3$^-$ adenoviral vector that contains an expression cassette in the E1 position containing containing the cytomegalovirus (CMV) immediate early promoter/enhancer, an artifical splice sequence, the human VEGF$_{121}$ DNA, and the SV40 poly A/stop signal. The AdVEGF$_{121.10}$ vector was manufactured according to procedures used to construct and produce Ad$_{GV}$CFTR.10 and Ad$_{GV}$CD.10 for two human clinical trials (i.e., U.S. FDA Clinical Trials BB-IND 5702 and BB-IND 6442). Following production of AdVEGF$_{121.10}$, the vector was purified and stored at −70° C. with a titer of between $2\times10^9$–$2\times10^{10}$ pfu/ml (i.e., $2\times10^{11}$–$2\times10^{12}$ pu/ml assuming 100 particle units/pfu) in a carbohydrate-salt solution.

An open chest cardiac bypass surgical procedure with routine cardiopulmonary bypass was carried out with the administration of the AdVEGF$_{121.10}$ vector following completion of the bypass procedure. The AdVEGF$_{121.10}$ vector was administered directly to the myocardium during open chest cardiac surgery using an insulin syringe with a 28 gauge needle. Two human patients, who were candidates for routine coronary bypass surgery and have diffuse or non-bypassable disease in at least one other coronary artery distribution, were given AdVEGF$_{121.10}$ administrations. For each of the two patients, the total dose ($1\times10^7$ pfu, $1\times10^9$ pu) of the vector was divided into 10 aliquots (100 $\mu$l /aliquot), with each aliquot administered to a site separated by 1.5–2.0 cm at a depth less than or equal to 5 mm.

The surgical procedures followed were such that the two patients fasted from food and liquids after midnight prior to the surgical procedure. A standard procedure was used by the cardiac anesthesiologist to prepare each individual and throughout the procedure. The individuals were transported to the operating room where standard monitors (three lead-modified EKG, pulse oximeter) were applied; premedications were administered as needed. Under local anesthesia, a radial arterial line was inserted for continuous blood pressure monitoring and blood sampling. Anesthesia was induced with midazolam, fentanyl, and/or thiopental. Supplemental anesthesia included midazolam, fentanyl, and/or thiopental, as well as isoflurane. Muscle relaxation was achieved with pancuronium. Succinylcholine was administered, as needed, for the facilitation of endotracheal intubation in which case an additional intravenous access was inserted. A central line (either internal jugular or subclavian vein) was inserted. Through that central line a pulmonary catheter was inserted to allow for monitoring of heart function (central venous pressure, pulmonary artery pressure, pulmonary artery wedge pressure, and computerized, thermodilution-calculated cardiac output). A transesophageal echocardiography probe was inserted to identify intracardiac structures and to assess valvular and ventricular function. A urinary bladder catheter was placed to measure urinary output. Anesthesia was administered at doses which permitted extubation within four to six hours upon conclusion of the procedure. The patients' chest was then prepped and draped in a standard sterile fashion using a betadine/alcohol solution. A small (approximately 0.6 mm radius, the same as a skin punch biopsy) skin biopsy was taken at the site of the skin incision. The biopsy was used for growing autologous fibroblasts for assessment of cytotoxic T-lymphocytes directed against the adenoviral vector.

A median sternotomy was performed and the saphenous vein, or another relevant conduit, was harvested. Followin median sternotomy, aortic and right atrial cannulation was performed after heparin administration (3 mg/kg). The left internal mammary artery was identified and dissected from the chest wall. The patient was placed on cardiopulmonary bypass as per standard practice. The cardiopulmonary bypass circuit included a Cobe Excel membrane oxygenator (Cobe Laboratories Inc., Lakewood, Colo.) and either a Cobe roller pump or a Biomedicus centrifugal pump (Biomedicus, Eden Prairie, Minn.). The circuit was primed with approximately 2200 ml of crystalloid solution (200 ml of 25% albumin, 0.5 mg/kg mannitol, 1800 ml Ringer's lactate). The coronary arteries to be bypassed were identified and marked. Following crossclaimping of the aorta, intermittent anterograde and/or retrograde cold blood cardioplegia with moderate systemic cooling (28–32° C.) was used. A myocardial temperature probe was placed to continuously monitor myocardial temperature during cardioplegic arrest, and the systemic temperature was monitored using a bladder temperature probe. Distal anastomoses to the coronary arteries using the reverse saphenous vein segments was performed, using running 7–0 Prolene sutures. The internal mammary artery was anastomosed in a similar fashion to the left anterior descending artery. The aortic crossclamp was removed, and the patient was systemically rewarmed to 36° C., utilizing the heat exchanger of the cardiopulmonary bypass circuit. Following initiation of rewarming, a partial aortic occlusion clamp was placed on the aorta. The sites of proximal anastomoses of the saphenous vein grafts were marked on the aorta, and 4.8 mm pledgets were excised from the aortic root. The proximal portion of each saphenous vein graft was anastomosed to the aorta using 6–0 Prolene sutures.

After completion of the proximal anastomoses, the 10 injections (100 μl/injection) of AdVEGF$_{121.10}$ were administered in an obstructed coronary artery territory not amenable to bypass. One patient had the vector administered to the right coronary artery distribution, and the second patient had the vector administered to the left ventricle. The patients were separated from cardiopulmonary bypass. Protamine was administered to reverse heparin-induced anticoagulation. The aortic and atrial cannulas were removed, and all cannulation sites were oversewn. Temporary ventricular pacing wires were placed. Thirty-six french thoracostomy tubes were placed in the left pleural space and mediastinum to provide post-operative drainage as per standard protocols. The sternum was reapproximated and closed using #20 wire. The fascia were closed in two layers using running 0 Vicryl suture. The skin was reapproximated with skin clips. A similar closure was employed upon the legs at the site of saphenous vein harvest.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method for enhancing the level of blood flow to muscle tissue comprising:
   directly injecting into the muscle tissue, via multiple injections to different points of the muscle tissue, a dose of a pharmaceutical composition comprising (a) a pharmaceutically acceptable carrier and (b) an adenoviral vector comprising a DNA encoding an angiogenic peptide, such that the level of blood flow to the muscle tissue is enhanced, wherein at least two of the multiple injections are administered within about 10 minutes.

2. The method of claim 1, wherein the method further comprises inducing angiogenesis in the muscle tissue.

3. The method of claim 2, wherein the muscle tissue is affected by a vascular occlusion.

4. The method of claim 1, wherein the muscle tissue is suffering from ischemia.

5. The method of claim 1, wherein the muscle tissue is within an organ.

6. The method of claim 5, wherein the organ is a heart.

7. The method of claim 6, wherein the heart is a human heart.

8. The method of claim 1, wherein one of the multiple injection is administered to up to 50 cm$^3$ of the muscle tissue.

9. The method of claim 8, wherein all of the multiple injections are administered within about 10 minutes.

10. The method of claim 9, wherein the multiple injections are simultaneous.

11. The method of claim 9, wherein the muscle tissue is heart tissue.

12. The method of claim 11, wheriein the angiogenic peptide is VEGF$_{121}$.

13. The method of claim 9, wherein the muscle tissue is in a limb.

14. The method of claim 13, wherein the angiogenic peptide is VEGF$_{121}$.

15. The method of claim 9, herein the angiogenic peptide is VEGF$_{121}$.

16. The method of claim 8, wherein the muscle tissue is heart tissue.

17. The method of claim 16, wherein the angiogenic peptide is VEGF$_{121}$.

18. The method of claim 8, wherein the muscle tissue is in a limb.

19. The method of claim 18, wherein the angiogenic peptide is VEGF$_{121}$.

20. The method of claim 8, wherein the angiogenic peptide is VEGF$_{121}$.

21. The method of claim 16, wherein the heart tissue is human heart tissue.

22. The method of claim 21, wherein the multiple injections comprise at least 4 injections.

23. The method of claim 22, wherein the multiple injections comprise at least 8 injections.

24. The method of claim 23, wherein the multiple injections comprise at least 15 injections.

25. The method of claim 21, wherein the angiogenic peptide is VEGF$_{121}$.

26. The method of claim 25, wherein the adenoviral vector is replication-deficient.

27. The method of claim 26, wherein the multiple injections comprise at least 4 injections.

28. The method of claim 27, wherein the multiple injections comprise at least 8 injections.

29. The method of claim 28, wherein the multiple injections comprise at least 15 injections.

30. The method of claim 26, wherein the adenoviral vector comprises at least a partial deletion of the E1 region of the adenoviral genome required for viral replication.

31. The method of claim 30, wherein the DNA is inserted into a region of the adenoviral vector such that, when transcribed, the direction of transcription of the DNA is opposite the direction of transcription of the region into which the DNA is inserted.

32. The method of claim 18, wherein the limb is a human limb.

33. The method of claim 32, wherein the multiple injections comprise at least 4 injections.

34. The method of claim 33, wherein the multiple injections comprise at least 8 injections.

35. The method of claim 34, wherein the multiple injections comprise at least 15 injections.

36. The method of claim 32, wherein the angiogenic peptide is $VEGF_{121}$.

37. The method of claim 36, wherein the adenoviral vector is replication-deficient.

38. The method of claim 37, wherein the multiple injections comprise at least 4 injections.

39. The method of claim 38, wherein the multiple injections comprise at least 8 injections.

40. The method of claim 39, wherein the multiple injections comprise at least 15 injections.

41. The method of claim 37, wherein the adenoviral vector comprises at least a partial deletion of the E1 region of the adenoviral genome required for viral replication.

42. The method of claim 41, wherein the DNA is inserted into a region of the adenoviral vector such that, when transcribed, the direction of transcription of the DNA is opposite the direction of transcription of the region into which the DNA is inserted.

43. The method of claim 1, wherein all of the multiple injections are administered within about 10 minutes.

44. The method of claim 43, wherein the multiple injections are simultaneous.

45. The method of claim 43, wherein the muscle tissue is heart tissue.

46. The method of claim 45, wherein the angiogenic peptide is $VEGF_{121}$.

47. The method of claim 45, wherein the heart tissue is human heart tissue.

48. The method of claim 47, wherein the angiogenic peptide is $VEGF_{121}$.

49. The method of claim 48, wherein the adenoviral vector is replication-deficient.

50. The method of claim 49, wherein the adenoviral vector comprises at least a partial deletion of the E1 region of the adenoviral genome required for viral replication.

51. The method of claim 50, wherein the DNA is inserted into a region of the adenoviral vector such that, when transcribed, the direction of transcription of the DNA is opposite the direction of transcription of the region into which the DNA is inserted.

52. The method of claim 43, wherein the muscle tissue is in a limb.

53. The method of claim 52, wherein the angiogenic peptide is $VEGF_{121}$.

54. The method of claim 52, wherein the limb is a human limb.

55. The method of claim 54, wherein the angiogenic peptide is $VEGF_{121}$.

56. The method of claim 55, wherein the adenoviral vector is replication-deficient.

57. The method of claim 56, wherein the adenoviral vector comprises at least a partial deletion of the E1 region of the adenoviral genome required for viral replication.

58. The method of claim 57, wherein the DNA is inserted into a region of the adenoviral vector such that, when transcribed, the direction of transcription of the DNA is opposite the direction of transcription of the region into which the DNA is inserted.

59. The method of claim 43, wherein the angiogenic peptide is $VEGF_{121}$.

60. The method of claim 1, wherein the DNA is inserted into a region of the adenoviral vector such that, when transcribed, the direction of transcription of the DNA is opposite the direction of transcription of the region into which the DNA is inserted.

61. The method of claim 1, wherein the angiogenic peptide is $VEGF_{121}$.

62. The method of claim 1, wherein the angiogenic peptide is $VEGF_{165}$.

63. The method of claim 1, wherein the muscle tissue is not suffering from ischemia.

64. The method of claim 1, wherein the muscle tissue is not affected by a vascular occlusion.

65. The method of claim 1, wherein the muscle tissue is in a limb.

66. The method of claim 1, wherein the adenoviral vector is replication-deficient.

67. The method of claim 66, wherein the adenoviral vector comprises at least a partial deletion of the E1 region of the adenoviral genome required for viral replication.

68. The method of claim 67, wherein the adenoviral vector comprises at least a partial deletion of the E3 region.

69. The method of claim 68, wherein the adenoviral vector comprises at least a partial deletion of the E1a region, at least a partial deletion of the E1b region, and at least a partial deletion of the E3 region.

70. The method of claim 66, wherein the adenoviral vector comprises at least a partial deletion of the E4 region of the adenoviral genome required for viral replication.

71. The method of claim 70, wherein the adenoviral vector comprises at least a partial deletion of the E1 region, at least a partial deletion of the E3 region, and at least a partial deletion of the E4 region.

72. The method of claim 1, wherein the multiple injections comprise at least 4 injections.

73. The method of claim 72, wherein the multiple injections comprise at least 8 injections.

74. The method of claim 73, wherein the multiple injections comprise at least 15 injections.

75. The method of claim 2, wherein the muscle tissue is human heart tissue.

76. The method of claim 75, wherein the multiple injections comprise at least 4 injections.

77. The method of claim 76, wherein the multiple injections comprise at least 8 injections.

78. The method of claim 77, wherein the multiple injections comprise at least 15 injections.

79. The method of claim 75, wherein the angiogenic peptide is $VEGF_{121}$.

80. The method of claim 79, wherein the adenoviral vector is replication-deficient.

81. The method of claim 80, wherein the multiple injections comprise at least 4 injections.

82. The method of claim 81, wherein the multiple injections comprise at least 8 injections.

83. The method of claim 82, wherein the multiple injections comprise at least 15 injections.

84. The method of claim 80, wherein the adenoviral vector comprises at least a partial deletion of the E1 region of the adenoviral genome required for viral replication.

85. The method of claim 84, wherein the DNA is inserted into a region of the adenoviral vector such that, when transcribed, the direction of transcription of the DNA is opposite the direction of transcription of the region into which the DNA is inserted.

86. The method of claim 2, wherein the muscle tissue is in a human limb.

87. The method of claim 86, wherein the multiple injections comprise at least 4 injections.

88. The method of claim 87, wherein the multiple injections comprise at least 8 injections.

89. The method of claim 88, wherein the multiple injections comprise at least 15 injections.

90. The method of claim 86, wherein the angiogenic peptide is $VEGF_{121}$.

91. The method of claim 90, wherein the adenoviral vector is replication-deficient.

92. The method of claim 91, wherein the multiple injections comprise at least 4 injections.

93. The method of claim 92, wherein the multiple injections comprise at least 8 injections.

94. The method of claim 93, wherein the multiple injections comprise at least 15 injections.

95. The method of claim 91, wherein the adenoviral vector comprises at least a partial deletion of the E1 region of the adenoviral genome required for viral replication.

96. The method of claim 95, wherein the DNA is inserted into a region of the adenoviral vector such that, when transcribed, the direction of transcription of the DNA is opposite the direction of transcription of the region into which the DNA is inserted.

* * * * *